United States Patent
Ehlgen et al.

(10) Patent No.: US 9,297,754 B2
(45) Date of Patent: Mar. 29, 2016

(54) METHOD AND DEVICE FOR DETECTING FOG USING SPECTROSCOPY

(75) Inventors: Tobias Ehlgen, Ravensburg (DE); Sebastian Van Staa, Leonberg (DE)

(73) Assignee: ROBERT BOSCH GMBH, Stuttgart (DE)

(*) Notice: Subject to any disclaimer, the term of this patent is extended or adjusted under 35 U.S.C. 154(b) by 611 days.

(21) Appl. No.: 13/581,562

(22) PCT Filed: Jan. 26, 2011

(86) PCT No.: PCT/EP2011/051026
§ 371 (c)(1), (2), (4) Date: Nov. 8, 2012

(87) PCT Pub. No.: WO2011/107308
PCT Pub. Date: Sep. 9, 2011

(65) Prior Publication Data
US 2013/0057687 A1    Mar. 7, 2013

(30) Foreign Application Priority Data
Mar. 2, 2010    (DE) .................. 10 2010 002 488

(51) Int. Cl.
*H04N 7/18*    (2006.01)
*G01N 21/53*    (2006.01)
*G01N 21/17*    (2006.01)

(52) U.S. Cl.
CPC ...... *G01N 21/538* (2013.01); *G01N 2021/1776* (2013.01); *G01N 2201/0216* (2013.01)

(58) Field of Classification Search
None
See application file for complete search history.

(56) References Cited

U.S. PATENT DOCUMENTS

| | | | |
|---|---|---|---|
| 6,587,573 B1* | 7/2003 | Stam et al. | 382/104 |
| 7,379,177 B1* | 5/2008 | Sones et al. | 356/239.1 |
| 2005/0270537 A1 | 12/2005 | Mian et al. | |

FOREIGN PATENT DOCUMENTS

| | | |
|---|---|---|
| CN | 1751391 | 3/2006 |
| EP | 1498721 | 1/2005 |
| EP | 1826648 | 8/2007 |
| EP | 2020595 | 2/2009 |
| EP | 2056093 | 5/2009 |
| JP | 51-049786 | 4/1976 |
| JP | 2002-286842 | 10/2002 |
| JP | 2008-170284 | 7/2008 |
| JP | 2009-025050 | 2/2009 |
| WO | WO 2004/076231 | 9/2004 |

OTHER PUBLICATIONS

International Search Report for PCT/EP2011/051026, dated Jun. 17, 2011.

(Continued)

*Primary Examiner* — Kate Luo
(74) *Attorney, Agent, or Firm* — Kenyon & Kenyon LLP (57) ABSTRACT

A method for detection or the density determination or the classification of an aerosol using spectroscopy includes: using an image taken by a camera for a vehicle, a first value of a parameter being ascertained from the at least one image in a first step, using a first color filtering, and a second value for the same parameter being ascertained in a second step having a second color filtering, which is different from the preceding color filtering, and the values ascertained in the at least two steps are compared, and as a function of the result of the comparison, the detection or the density determination or the classification of the aerosol is carried out.

17 Claims, 3 Drawing Sheets

(56) References Cited

OTHER PUBLICATIONS

Stephen . Metzger, et al., "Techniques for Identifying Dust Devils in Mar Pathfinder Images", IEEE Transaction on Geoscience and Remote Sensing, IEEE Service Center, Piscataway, NJ, vol. 38, No. 2, Mar. 1, 2000 pp. 871-872.*

Huo et al., "Cloud Determination of All-Sky Images Under Low-Visibility Conditions", Journal of Atmospheric and Oceanic Technology, American Meteorological Society, Boston, MA, vol. 26, No. 10, Oct. 1, 2009, pp. 2172-2181.*

Cantor et al., "MOC Observations of the 2001 Mars planet-encircling dust storm", Icarus, Academic Press, San Diego, CA, vol. 186, No. 1, Dec. 8, 2006, pp. 60-96.*

Livingston, et al. "Airbourne Sun Photometer Measurements of Aerosol Optical Depth and Columnar Water Vapor During the Puerto Rico Dust Experiment and Comparison with Land, Aircraft, and Satellite Measurements", Journal of Geophysical Research, vol. 108, No. D19, Jul. 2, 2003, pp. 4-1-4-23.*

* cited by examiner

METHOD AND DEVICE FOR DETECTING FOG USING SPECTROSCOPY

BACKGROUND INFORMATION

1. Field of the Invention

The present invention relates to a device and to a method for detecting fog using spectroscopy.

2. Description of the Related Art

For the detection of interference with visibility in a vehicle, that is caused particularly by fog, some methods exist in the related art for detecting fog.

A device is known from published European patent application document EP 1498721 A1 which takes images in the travel direction, using a camera in a vehicle. An image of this camera is evaluated as to whether there is at least one pixel which falls below a brightness value, i.e. is dark. Because of the scattered light effects when there is fog present, one may assume that all pixels have a minimum brightness, and consequently permit the conclusion that there is fog.

Furthermore, camera systems are known for use in a vehicle for detecting fog, which require an active element (such as infrared-LED), for example published European patent application document EP 2020595 A1.

Another method is the detection of fog based on the detection of objects and perhaps their distance. Published European patent application document EP 1826648 A2 compares the edge thickness of detected objects with those in a database, and derives from this the visibility conditions and rain or fog. This works only as long as objects are present and these are described in the database.

A more detailed method is described in published European patent application document EP 2056093 A1, in which the gray values distribution is examined in a certain area of the image, particularly on the horizon. However, this method may lead to false detection in the case of other weather conditions that result in the same physical effect on the image, a possible example for this being snow cover on the landscape and the road.

Moreover, there is voluminous non-patent literature that also speaks to the topic of fog detection.

Up to now, there does not, however, appear to exist fog detection using image-generating methods (video), without the distance (visual range) being determined, especially the distance from other objects or at least a hypothesis on this.

BRIEF SUMMARY OF THE INVENTION

By contrast, the method according to the present invention has the advantage that, by evaluating the spectral properties of aerosols, a measuring method becomes possible that is sufficient without active illumination, determination of a distance or visibility range or a special sensor system exclusively for aerosol detection. The illumination is able to take place passively by ambient brightness or extraneous light sources.

The physical effect on which the method is based is the increased absorption of light while it is penetrating through aerosols, where the light rays are absorbed on the particles or molecules (e.g. water) or are refracted. This absorption and dispersion is a function of the wavelength, however, as one will realize by the fact that fog generates a relatively cold light, i.e. high color temperature. This effect may be detected by observing the color content in the video image, and then evaluated.

The possibility, that results from this optical condition, is also advantageous of distinguishing aerosols from other objects or structures in the image, and furthermore or alternatively also of determining the type and/or the density (concentration) of the aerosol. The method according to the present invention is carried out by doing this, using images acquired by an image-generating method. According to the present invention, either at least two images are present having different color information, or the information is ascertained from one image, for instance, using known color-extracting methods from an RGB image or, for example, in the case of an image acquired using an R3i camera, by masking the respective red pixels or the non-red pixels (gray pixels). The color filtering may be implemented by hardware technology measures (within the scope of taking the picture) such as a corresponding color filter in front of the objective or parts of the objective or in the optical beam path or by a color mask over the pixels of the imager. Filtering may also be implemented by software technology measures (within the scope of image processing), by extracting the desired color channels or color spectra from a color image.

The at least one image to be evaluated has to record a scene in which an aerosol is able to be detected or to be visible, that is, in such a way that a certain optical depth is assured, so that dispersion effects and absorption effects, with their different spectral properties, come into effect in such a way that they have their effect in the at least one image and are measurable. Thus, a camera alignment seems to be more meaningful if it is aligned with the width (e.g. of the horizon/of the landscape), instead of with the ground, provided there is such a small distance between the camera and the ground that the fog would be visible only negligibly. The method is suitable for application in a motor vehicle, in which a camera has often already been installed these days for other driver assistance functions, which now can additionally take on the task according to the present invention, without additional (substantial) costs being created for hardware.

The at least one image should now be filtered in such a way that at the end, at least two (virtual) images exist which include different color data. Depending on the optical or spectral properties of the aerosols to be detected, the color band to be filtered may be greater or smaller, perhaps even limited to one single light frequency. The second (virtual) image must in any case have a different color information than the first. Accordingly, the filter also has to be developed differently. Instead, one may also do without the use of a second color filter and possibly even use the original image using all the color information (or the gray information).

If the spectral distinction features of the one or more aerosols require detailed color spectroscopy, this method does not necessarily have to be used with the described two images, or only two color filtrations, but, corresponding to necessity and the number of color ranges to be analyzed, may be multiplied. From these virtual images, i.e. the images after color filtering, one color parameter is now ascertained in each case, which is of the same type but has the property, in the case of an aerosol or various aerosols of assuming a different value for the extraction from the respective image. If possible and suitable, the determination of the virtual image may also be omitted if the desired parameter is also able to be ascertained without this step, for instance, directly from the original image.

The values of the parameters ascertained are compared to one another in a suitable manner, so that it is possible to detect whether, depending on the application, an aerosol is present at all, a certain aerosol is present, which aerosol is present and/or what density (concentration) the aerosol has.

Advantageously, if fog or an aerosol having high dispersion or back reflection occurs, self-glare is able to be avoided which would be created if, for example, a wall of fog were lit up by a high beam of headlight and the reflecting light dazzled the driver.

Using the method according to the present invention, an aerosol may advantageously be determined more accurately and faulty interpretations, as have frequently occurred up to now, may be avoided if, for example, snow covers the roadway, the camera takes this and the image then looks similar to visibility conditions during fog.

The method may advantageously be used for certain aerosols, such as fog, in that the first color filtering determines the red portion in the image and a second color filtering does not take place, so that in this case the gray portion is determined. The red filter may be developed in such a way that it is only transmitting for exactly one wavelength in the red region, or for a whole frequency band in which at least a part of the red spectrum is located. The virtual gray image having the gray portion, depending on the device, may be taken over directly from the original image or ascertained, for example, by cancellation or averaging of the color information, if there is a color image in the original. In the case of a device such as an R3i camera, this may be done by masking out the respective pixels, one mask filtering the red pixels and masking out the others, and the other mask filtering the gray pixels and masking out the red pixels, or is not present because the pixel sensors supply the gray value directly.

In addition to these two color filterings, additional filtering possibilities and evaluation possibilities may be added. Thus, additional blue filtering is conceivable, by which a plausibility check of the results may be carried out. Thus, upon detection of fog, the red portion would experience strong filtering, since fog absorbs particularly strongly in this frequency range, and, by contrast, absorbs correspondingly less in the blue region.

As parameter, the average brightness value of the pixels of the image is advantageously selected. The light intensity (brightness) between the image color filtered in the one or the other manner is thus able to be determined, so as later to carry out the comparison with it. Since an aerosol usually appears as a planar diffuse manifestation, and causes an image that is poor in contrast, the average value of the brightness values of the pixels is formed. The spectral intensity distribution of the image having the supposed aerosol is thereby ascertained.

Alternatively, one may also select as parameter the average gradient of the pixels of the image. The gradient of two pixels is determined from the difference in their brightness value. This gradient is now averaged so as thereby to obtain a measure that reflects the contrast. A planar gradient is typical for fog. A high gradient would be an indication that in a part of the area of the image there is a lit up traffic sign or the like. The presence of such objects could lead to an erroneous detection of fog, as soon as high red portions (based on their reflection characteristics) are present in the partial area. The evaluation of the gradient criterion prevents this by suppressing the fog message at high gradients. The gradient formation between the pixels, as is known, may take place in one or two directions or possibly even more directions (which are then averaged), in order to be able to determine not only the contrast in one direction, but the contrast free of directions.

For this method, advantageously a relatively low computing capacity is required compared to other methods which, for example, have to carry out an object determination or evaluate an image history.

The at least two values of the parameter are advantageously evaluated by difference formation. Thereby the comparison described of the two parameter values is carried out. Usually, this difference is compared to a threshold value, at whose exceeding or undershooting an aerosol is detected or not detected.

The difference may also (if necessary without observing the threshold value) be a measure for the density of the aerosol. The density (concentration) is proportional to the number of fog droplets per volume unit.

Different threshold values or value ranges of the difference may supply a conclusion on the type of aerosol, and with that, a classification. Which threshold values, or boundaries or connections exactly are used for this depends on the physical properties of the respective aerosols that is to be determined.

If the method is used exclusively at night, for instance, to prevent turning the headlight to full beam in fog, observing the difference is sufficient.

Instead of forming a difference, forming the quotient of the two parameter values is also conceivable. Observing the quotient would also have the advantage that a comparison to a given threshold value may also take place at different light conditions (day/night), since this value has the effect of independence from the brightness range, since the brightness level almost cancels out during the quotient formation. Consequently, the quotient tells what portion of a color is present in the gray image.

Moreover, a variance may also be formed from these values. The variance may be drawn upon as a quicker determination of the structuredness of the image. It is defined as the arithmetic mean of the squared distances of a quantity of measured values (in this case: pixel-brightness values) from their average. It would thus be meaningful to calculate the variance of the brightness values of the pixels in the red image, as well as the variance of the pixels of the gray image (or that of each desired color channel in RGB). If these values are greater than a threshold value, one may assume a structured scene, which is an indication that no aerosol is involved. In particular, in this case, one should concentrate on the variance of the gray values from the average value, which corresponds to the frequency in the image.

Furthermore, a comparison may also be carried out using a combination of the gray value distribution information. What is involved is the distribution of the gray values and the red values, respectively, (if a Gaussian distribution is assumed, it means the variance and the average value).

To carry out the comparison, the analogous applies as described above for the example of the difference.

The checking according to the present invention may advantageously be carried out by a comparison of the parameter values to an additional threshold value. In this case, the difference of the parameter values is checked against a second threshold value which lies above the first threshold value, that is, it is exceeded when, for instance, the brightness of the gray value is even greater than that of the red value. This supplies a conclusion about possible overexposure, or large brightnesses, for example, by undesired reflections (of one's own headlight on signs, for example), or active light sources (e.g. headlight of an oncoming vehicle), which, if one were using only one threshold value, would also be classified erroneously as an aerosol. This may occur, for example, if behind a crest in the road ahead a vehicle is coming on and its headlights suddenly become visible.

Using the variant of quotient forming from the brightness between the gray value and the red value, however, this is not possible.

Advantageously, the aerosol (or the aerosol that is perhaps present) is lit up using one or more headlights. Such light sources have their own spectral characteristics, whereby, by a skilled choice of a suitable headlight, based on its internal spectral characteristics, the physical effect, already described, for aerosol detection is reinforced, and consequently detection is made easier. This may occur either passively, in that only a suitable headlight is picked, or actively, in that the spectral characteristic of the headlight is taken into account during the evaluation.

The spectral characteristic of the headlight designates the spectrum the headlight emits, i.e. which wavelengths at which intensities. The taking into account during the evaluation may be done in that, for example, threshold values are adjusted or a suitable comparison method is selected, or a certain parameter is determined which complies with the special characteristic of the selected headlight.

Advantageously, a convolution takes place of the spectrum of the selected headlight with the absorption characteristic of an aerosol to be detected. The spectrum of the headlight is known, just as is the spectrum (or inversely, the absorption characteristic) of an aerosol that is to be detected. Because of the convolution (as it were, a multiplication of the damping of the individual wavelengths—known from the signal processing), the expected spectrum is able to be ascertained which should appear in the image if a corresponding aerosol is present. As was described in an exemplary manner, for a discrete evaluation, the threshold values for individual wavelengths are now able to be ascertained as a function of the aerosol and the headlight. A complete spectral evaluation is naturally possible in exactly the same manner. By taking into account the headlight characteristics, an accurate determination is able to be carried out. If it is to be determined of what type the aerosol in the image is, for each possibly occurring (or to be detected) aerosol this convolution with the spectrum of the headlight has to be carried out, whereby a plurality of threshold values, and thus classes, come about and the comparison to the actually appearing spectrum in the image makes possible a classification.

For fog detection especially (possibly also for other aerosols) xenon headlights or headlights made up of LED elements, would be well suitable, since they have a reinforced bluish spectrum which, convoluted with the spectrum of fog, would show clear damping in the red region. This damping is clearer than would be created if the fog were lit up using white light.

The ascertainment of the parameters is expediently carried out only by taking into account a cutout of the image. If the selection of a suitable, sound image cutout is successful, the calculating load and the calculating time become less, and resource savings are made possible.

The selection of the cutout of the image (the region of interest—ROI) is successful if in it as good an illumination as possible is given by the headlight. The effect to be observed, i.e. the difference between the average red value and gray value is highest when as large as possible an area of the ROI is lit up as strongly as possible. For this reason, the bright-dark boundary should lie outside the ROI, if possible. The bright-dark boundary is the line specified by the headlight, in which the lit-up region goes over into the dark, non-lit-up one.

In one refinement, the image cutout is able to be selected not only in a fixed manner in the image, but is able to adjust adaptively to the environmental conditions. Thus, it is conceivable, optionally still to take into consideration a roadway model or the topology (such as curves, crests or hollows), and to select the cutout in such a way that the aerosol detection is carried out in an area which is meaningful for the further course of travel.

Since it may be very meaningful to, place the cutout into the abovementioned lit-up area, there is available the tracking of the cutout to a possible adaptive headlight (headlight leveling, cornering light).

The cutout is also able to move uniformly to the steering wheel/steering angle, just as does the adaptive cornering light. In this instance, the basic idea is supported according to which the cutout should be selected which is brightened most strongly by the light, since in that place, there is the greatest effect of spectral suppression of the red value (by fog).

The plausibility check of the aerosol detection, described according to the present invention, is advantageous when using further data which give information on aerosol being present.

Since a faulty detection should never be excluded free from doubt, and interfering effects, such as extraneous light sources having unknown spectra may have a corrupting effect on the result, such a measure is meaningful. By such a plausibility check, false positive detection of aerosols is able to be further limited.

A plausibility check may be carried out using known methods, for instance, using those described in the related art, or others, such as a visibility determination, in which the presence of an aerosol is excluded as of a certain visibility. Furthermore, a plausibility check is able to take place using a gradient determination, this never detecting an aerosol if the average gradient in the image (ideally a gray image) exceeds a certain threshold value, which means an abundance of high contrast (i.e. structure in the image) has to be present, which cannot be reconciled with an aerosol of a certain density. Moreover, one or more external light sources are able to be detected for the plausibility check, and, if necessary, it may be determined whether these have a halo or corona. If this is not the case, there may be present an aerosol between this light source and the camera.

To detect whether a glare is a self-glare, such as by fog, or an extraneous glare, such as by other vehicles, an object recognition may be drawn upon, for example, which perhaps recognizes the other vehicles. Even a reflection at flood-lit signs could erroneously be detected as fog. In this case, too, a plausibility check using an object detection would help.

The detection of an aerosol is meaningfully able to be used advantageously for a multiplicity of purposes in the vehicle. The information on the presence of an aerosol or a certain aerosol or its concentration may be meaningfully used to effect positively safety functions, comfort functions, driver assistance functions or drive train functions.

If, for example, an aerosol hindering visibility is detected (e.g. fog), an advantageous light distribution may be activated (in the case of fog, for example, deep, wide lighting up in front of the vehicle). If no fog is detected owing to the method according to the present invention, although, for instance, the image demonstrates a closed snow cover on the roadway, which could normally not be distinguished from a wall of fog, the light distribution, in contrast, is not changed or it is set so that it is useful for far visibility. In this case, the high beam could be activated or kept on, of course while taking into account additional known boundary conditions such as avoiding the glare of oncoming traffic, etc.

The automatic activation and deactivation of a fog tail light or an adverse-weather light is conceivable without further consideration.

Using the example of light controlling, it is shown how a plausibility check is made possible even for activating a vehicle function. Thus, one may do without changing the headlight setting even when fog is detected (poor visibility) if it is daytime and not night. This may be ascertained, for instance, by using a light sensor (implementable also as a function using the camera described or classically as an independent sensor) and a threshold value. Furthermore, a change in the headlight setting may be omitted if the speed of the vehicle is low, and does not exceed a threshold value.

If the method is used for light controlling and at the same time the undesired effect of illumination by an oncoming vehicle sets in, which could possibly falsify the fog detection, this would not have any effect, since, in this case, one should dim anyway. At least the light control would therefore be partially immune against such undesired effects.

Safety systems such as seatbelt tensioners, air bags or braking assistants/braking systems could in a suitable manner be prestressed or alarmed, when an increased accident potential (as in poor visibility) is to be assumed.

Comfort systems could switch over from outside air to recirculating air or could activate (air) filters when certain aerosols, such as smoke, industrial gases have been detected.

Driver assistance systems could classify the data that they ascertain from the video image, under poor visibility conditions, as less relevant or usable than, for instance, the data from other sensors (e.g. radar, ultrasound).

The drive train may be influenced to the extent that the rotational speed is increased, for example, so as to enable stronger engine braking or to generate a louder travel noise which could warn the surroundings of the approaching vehicle.

Speed and/or steering interventions may be carried out to avoid local aerosols or, in the case of fog, to lower the speed or emit a warning. This may be done in combination with data from a navigational system that is able to judge avoidance possibilities or the driveability of terrain lying ahead.

As a function of the type of aerosol, a warning may be issued before the aerosol or an emergency call, for instance, if it is poisonous.

Explanation of Terms

Spectroscopy or spectrometry is a group of observation methods which, with the aid of spectra (color dispersion) of light sources (and also the image to be analyzed) investigate how electromagnetic radiation and matter interact. One examines at which frequencies or wavelengths a substance is able to absorb or emit energy in the form of light quanta or electromagnetic waves. This color dispersion may be carried out using one or more filterings.

The image-producing method required for the present invention may be implemented by a camera system having the following properties: It has to supply images that are suitable for color filtering. This may be a classical RGB camera or an R3i camera, for example. In the case of the latter, every 4th pixel is provided with a red mask, and thus takes only the red portion (selective pixel coloration). Thus, when viewing only these pixels, a red image appears, and a gray image when viewing the others. Alternatively, one may also use a camera system having 2 monocameras or several optical paths having different filtering, or even a stereocamera whose 2 light paths run through different filters.

An aerosol is a mixture of solid and/or liquid floating particles and a gas, which may be of different origins. Particles of primary aerosols usually originate from mechanical or thermal processes. In secondary aerosols, the particles have formed from gaseous substances by chemical reaction and/or by adsorption of the reaction products on condensation nuclei. Aerosols may, of course, have organic components (pollen, spores, bacteria), natural inorganic components (dust, fine dust, sand, smoke, sea salt, water droplets), combustion products introduced by humans (smoke, cigarette smoke, exhaust gases, industrial gases, dense smoke, soot or oil fumes (e.g. from a car exhaust), ash or dusts or nanoparticles produced by people.

The term hydrometeor is the generic term used in meteorological terminology for all forms of condensed water (combining form "hydro"), that are observed in the atmosphere (combining form "meteor"), that is, all liquid and frozen particles of water. Other solid and liquid components of the atmosphere, in whose composition water plays no, or at least almost no part are designated as aerosols. Accumulations of hydrometeors are damp fumes, froth, condensation trails, fog, drizzle, rain, drifting snow, clouds and others.

According to the present invention, hydrometeors (or their accumulations) are also being claimed when aerosols are mentioned. Whether hydrometeors are delimited from aerosols, or represent a subgroup of these, is partially contradictory in the literature.

In physics, the transformation of vibrational energy into another form of energy is designated as damping. This is given expression, for example, in the decaying of a signal, a vibration or a wave. Electromagnetic waves are damped in the atmosphere. In the absorption of light, the energy taken up is not only converted to heat, but may also become lost to aerosols by other mechanisms, such as fluorescence, as well as by scattering. In the present instance, the terms absorption and damping have a similar meaning. By contrast, the transmissivity corresponds to the inverse, namely the transmission for light (frequency-dependent) in an aerosol.

DETAILED DESCRIPTION OF THE INVENTION

Figure 1:
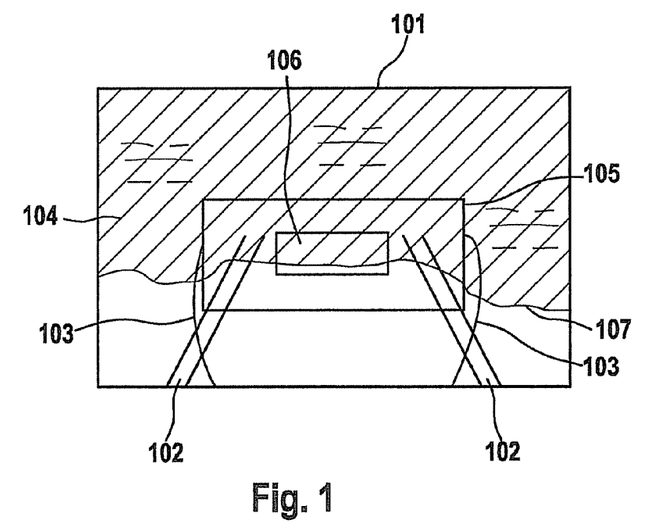
FIG. 1 shows an image taken by a camera having a fogy scenario.

FIG. 1 shows an image 101 as it might have been taken by a camera in the vehicle, in foresight. A fog scenario having the fog or fog wall 104 visible, into which lane marking 102 runs and is less visible with increasing distance. Near to the vehicle, light cone 103 leads to a partial illumination of the scenery, and with increasing distance, to an illumination of the fog 104, the light being scattered back by the latter, and it may lead to glare, above all in glare region 105. By limit of visibility 107 a virtual line is defined up to which lighting up may be meaningful. In reality, this line will not be able to be sharply imaged, based on the continuous optical properties of the fog. The application of the method according to the present invention may, for instance, be limited to the cutout of measuring region 106 (region of interest, ROI) which, ideally, is at the visibility or bright-dark border or includes it.

Figure 2:
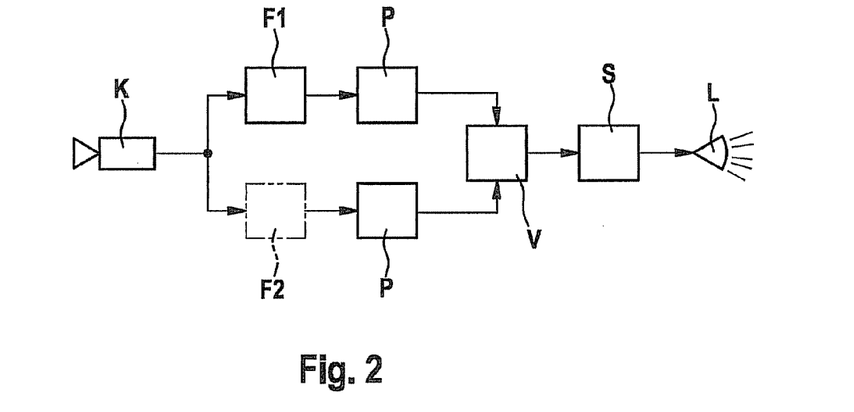
FIG. 2 shows a block diagram illustrating the method and device according to the present invention).

FIG. 2 explains the method and device according to the present invention, wherein starting from video camera K, which is able to supply an image 101, a filtering F1 is carried out which brings about a (virtual) color image having desired color information. In this embodiment, F1 is a filter, which preferably filters out the frequency portions that do not lie in the red region. Filtering F1 supplies a so-called red image or the red portion. Two additional color filterings F2 may optionally have application. In the execution described for fog detection, however, the original gray image is also suitable so that no second color filtration has to be undertaken. From the two images ascertained by F1 and F2, respectively, the value of the same parameter P is ascertained. In particular, the average brightness value of the pixels of measuring region 106 in its respective color filtering is able to be F1 and F2, or rather only F1. In this case, in each case a scalar value $M_G$, $M_R$ would be yielded, which represents the average brightness, and is evaluated in a comparator V, for instance, by a difference formation D of the two scalars $M_G$, $M_R$ and a test of whether this difference exceeds or falls below a certain threshold value. In the case of the fog detection, if the difference between the average value of the brightness of the gray image and the average value of the brightness of the red image exceeds a certain value, the presence of fog would be assumed.

The abovementioned checking of the difference against a second threshold value is not shown here, but it may also be carried out at this point.

The selection of a suitable threshold value comes about from empirical trials or physical considerations. Now, if fog has been detected, a control unit S, which is responsible for the light control, is able to actuate headlights L accordingly. In particular if a supposed glare (i.e. a great brightness in the image and in glare region 105) takes place, it has to be checked whether there is fog present and consequently there is glare, and not a brightly illuminated scenery, which, in turn, would be desirable. If fog were detected, the headlight could be deactivated and/or the fog light could be activated.

FIG. 3 shows the physical relationship graphically.

Figure 3A:
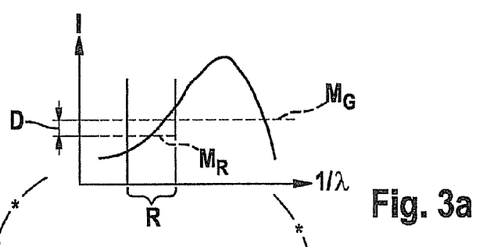
FIG. 3 shows a spectral analysis with and without a fogy scenario.

In FIG. 3a, the spectrum is shown of a xenon headlight, whose intensity or brightness I in the blue region, i.e. in regions of higher frequency or shorter wavelength A is greater than in the low frequency (red) region. To this spectrum one may assign an average value of the intensities over all frequencies, which corresponds to the average gray value MG. A red filtering according to the present invention may be developed in such a way that it only takes into account spectral band R, which means essentially that it filters out all the frequency portions that do not lie in spectral band R. To the brightness values in this spectral band R, an average brightness value $M_R$ may also be assigned as the average value of the intensities over all frequencies in band R. The two spectral brightness values $M_G$ and $M_R$ differ by a difference D. This difference changes as a function of the presence of a fog, as will be shown below. The comparison according to the present invention is made possible because of the evaluation of this difference. Alternatively, between these average brightness values, the quotient or other combinations described in the present invention may be formed.

In partial Figures b) and d) we now show the continuation of the scenario in the case of the presence of fog, and in partial Figures c) and e) the continuation of the method when there is no fog.

Figure 3B:
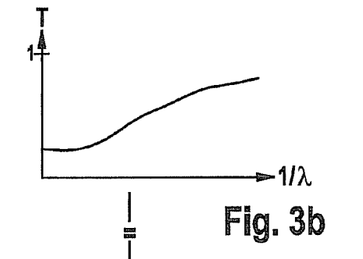
Figure 3C:
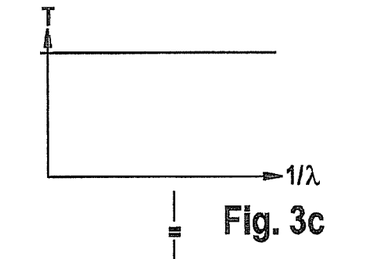

In partial Figure b), the spectral transmission characteristic of fog is shown, a higher damping (lower transmissivity T) appearing in the lower frequency region, e.g. the red region, and a lower damping for higher frequencies. In Figure part c) the trivial case is shown of good visibility, i.e. no damping.

Figure 3D:
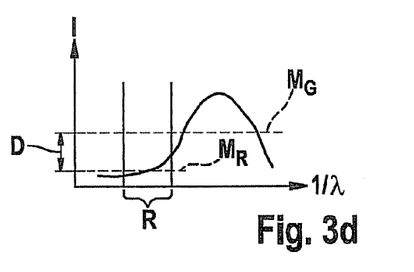
Figure 3E:
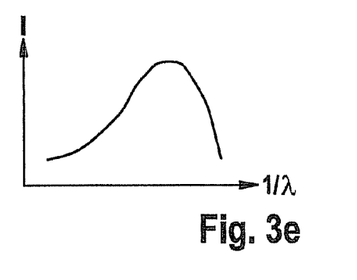

Now, if these absorption characteristics are a) convoluted* with the headlight spectrum in Figure part a), the intensity curves shown in Figure parts d) and e) result, the curve in Figure part e) corresponding to the original one in Figure part a) since no damping (1/T) has taken place. Influences by the image motive or other light sources are not to be taken into account in this instance. Based on the dynamic image changes, these should average out during a locomotion.

In Figure part d) the spectral curve to be ascertained in the image of the taking camera is shown, if, using a headlight corresponding to Figure part a), the image was taken in response to the presence of fog, having a damping characteristic as in Figure part b). The ascertainment carried out in this instance of the average values of brightness MG and MR is ascertained from the image according to the method of the present invention.

The (uninfluenced) average values of the brightness occurring in Figure part a) for the headlight are already yielded by the known characteristic of the headlight and are known. Since, during operation, they cannot be measured via the camera, they may be stored/configured for evaluation, and improve the method according to the present invention.

Thus, the effect of the fog is clearly visible in an increase in the difference of the average values V of Figure part d) compared to Figure part a).

Figure 3F:
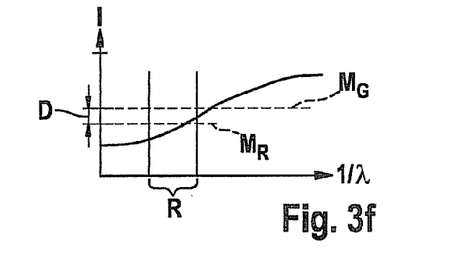

In contrast, in Figure part f), the spectral distribution is shown, that is discerned in the image, as it would be measured if the characteristic of the headlight were not known or had no overweighted spectral portions, or no headlight were switched on (e.g. in the daytime). In this instance, the difference V of the average values of the brightnesses would be measurable, to be sure, but what is detectable is the reinforcement or rather the increase in the difference in response to the use of corresponding headlights, as shown in Figure parts a) and b). Because of the reinforced effect of the headlights having known characteristics, the threshold values for a fog detection, for example, may be selected to be larger, so that fewer false fog detections take place.

Conversely, it has to be taken into account that such headlights may have the effect that a scenery taken in the picture is also able to have, in a reinforced manner, the spectral characteristics of the headlights without fog, which again could damp this effect. Empirical tests, however, have been able to confirm that advantage.

Figure 4:
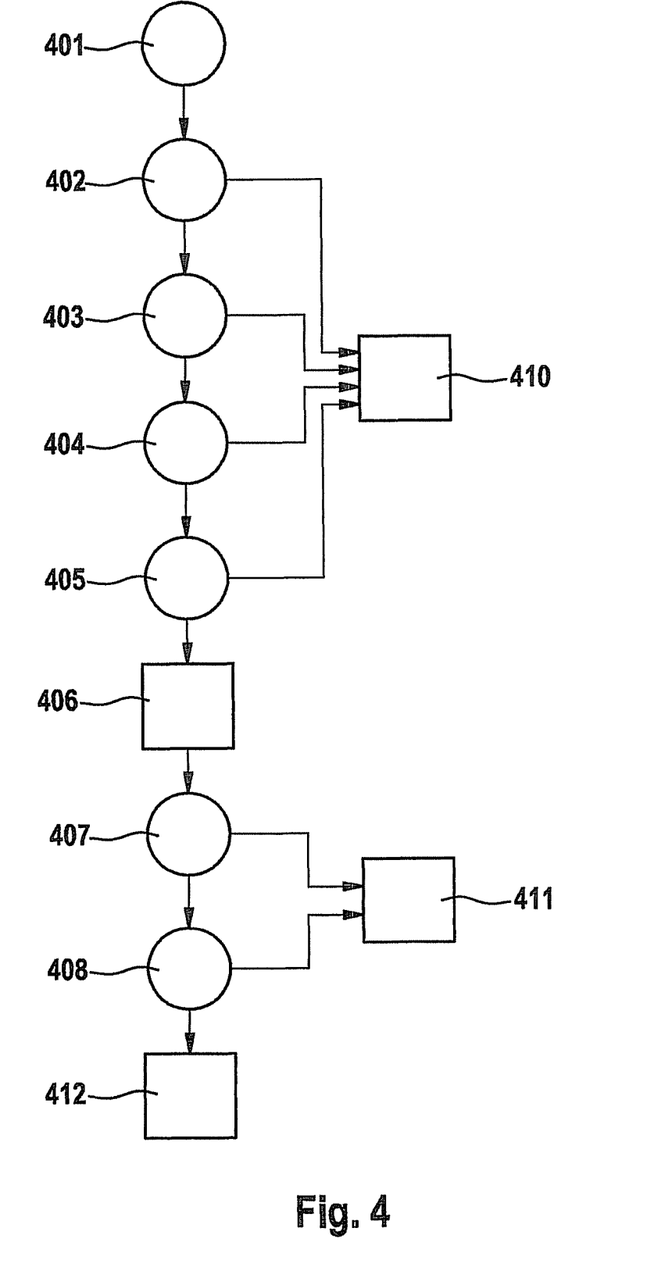
FIG. 4 shows a flow chart for a light control using the fog detection according to the present invention.

FIG. 4 shows a flow chart such as might be implemented for a light control, the method according to the present invention finding application for fog detection. The system starts at starting point 401 which, for example, is able to be called up iteratively at certain time intervals. The elements and tests may also be used selectively, and in the same way, additional meaningful points may be fitted into the sequence or the order of the sequence may be changed.

A visual range determination 402 is performed which, for example, may be implemented in that, for example, it is checked whether the forward-viewing distance exceeds a threshold value, and if yes, it is assumed that no fog is present 410. The forward viewing distance may be determined, for example by a lane detection algorithm, and if the lane (marking) is still visible at a sufficiently far distance, then the visibility distance is sufficiently good.

If the visibility distance is regarded as being too low, a contrast determination 403 is carried out which, for example, is able to be implemented in that a gradient determination is performed, and the average gradient in the gray image having to exceed a certain threshold value. If it does that, that is, an appropriate contrast is present, one may assume that no fog 410 is present. If a self-glare appears nevertheless, it may originate with reflecting signs. Consequently, a distinguishing of the cause of the glare is possible.

If, on the other hand, the contrast is also too low, one may carry out in addition a light source detection 404 (external light sources) and in the case of the occurrence of such a one it is checked whether it has a halo or a corona. If this is not the case, that is, the light source is clear and clearly visible, one may assume that no fog 410 is present.

If yes, however, then going further, one may apply the method according to the present invention of spectroscopic fog detection 405 which, as described, is able to detect the non-presence of fog 410 or the presence of fog 405. Up to this step 406, the method was treated for fog detection, but in what follows, the method is used for light control.

If fog 406 has been detected, a night detection 407 checks whether it just happens to be nighttime or not, in that the light quantity through a light sensor exceeds a certain threshold value. If it is daytime, no headlight setting or change of setting 411 is carried out since, when the light is active, this could possibly represent a conscious desire/setting of the driver.

If it is nighttime, a speed check 408 is carried out, which, as it were, represents a safety circuit, so that, at low speeds (e.g. <50 km/h) no change in the headlight setting 411, in particular, no activation of the high beam takes place. If however, a certain minimum speed is attained or exceeded, then in the case of the presence of fog, the fog light should be activated.

If no fog 410 is detected, the high beam may be activated, for instance, in case additional boundary conditions are present (such as no oncoming traffic). Rapid changes between detected fog and non-detected fog may be debounced, so that the headlight setting does not permanently keep changing or begins to flicker. A fog tail light may be similarly controlled.

What is claimed is:

1. A method for performing one of detection, density determination, or classification of an aerosol in an environment using at least one image of the environment taken by a camera of a vehicle, comprising:
    in a first step, ascertaining a first value of a selected parameter of the at least one image using a first color filtering;
    in a second step, ascertaining a second value of the selected parameter one of: (i) without the first color filtering, or (ii) using a second color filtering different from the first color filtering;
    comparing the ascertained first and second values; and
    performing, as a function of the result of the comparison, the one of detection, density determination, or classification of the aerosol,
    wherein:
        the selected parameter is one of the average brightness value or the gradient of the pixels,
        the comparison of the first and second values is achieved by formation of at least one of a difference, a quotient, and a variance using gray value distribution data,
        the comparison of the first and second values is achieved by formation of a difference between the first and second values,
        the difference is compared to a first threshold value and a second threshold value higher than the first threshold vale, and
        the aerosol is one of detected or classified if the difference is higher than the first threshold value and lower than the second threshold value.

2. The method as recited in claim 1, wherein the aerosol is illuminated using vehicle headlights, and the spectral characteristic of the vehicle headlights is taken into account in the one of detection, density determination, or classification of the aerosol.

3. The method as recited in claim 2, wherein the result of the comparison is subjected to a second comparison against a predetermined expected result for the case of non-presence of an aerosol.

4. The method as recited in claim 2, wherein the method is used for at least one of (i) regulation of illumination range of the vehicle headlights, (ii) light distribution of the vehicle headlights, and (iii) influencing of one of a vehicle safety function, a driver assistance function or a drive train function.

5. The method as recited in claim 1, wherein the ascertainment of the first and second values of the selected parameter takes place by taking into account only a selected portion of the image.

6. The method as recited in claim 5, wherein the selection of the selected portion of the image satisfies at least one of the following conditions: (i) the selected portion includes best illumination by the headlight; (ii) the location of the selected portion of the image is changed depending on the steering angle; and (iii) the selected portion of the image is set corresponding to the surface topology of the scenery located in the image.

7. The method as recited in claim 1, further comprising:
    checking the aerosol detection for plausibility using additional data.

8. The method as recited in claim 1, wherein the first color filtering determines a red portion of the at least one image, and an absence of the first color filtering determines a gray portion of the at least one image.

9. A method for performing one of detection, density determination, or classification of an aerosol in an environment using at least one image of the environment taken by a camera of a vehicle, comprising:
    in a first step, ascertaining a first value of a selected parameter of the at least one image using a first color filtering;
    in a second step, ascertaining a second value of the selected parameter one of: (i) without the first color filtering, or (ii) using a second color filtering different from the first color filtering;
    comparing the ascertained first and second values; and
    performing, as a function of the result of the comparison, the one of detection, density determination, or classification of the aerosol,
    wherein the selected parameter is one of the average brightness value or the gradient of the pixels,
    wherein the aerosol is illuminated using vehicle headlights, and the spectral characteristic of the vehicle headlights is taken into account in the one of detection, density determination, or classification of the aerosol, and
    wherein a convolution of the spectrum of the headlight with absorption characteristic of at least one possible aerosol is carried out, and the aerosol is detected as a function of the convolution.

10. A device for performing one of detection, density determination, or classification of an aerosol in an environment using at least one image of the environment taken by a camera of a vehicle, comprising:
    a parameter determination unit having at least a first color filter and a second color filter different from the first color filter, wherein the parameter determination unit is configured to:
        ascertain, in a first step, a first value of a selected parameter of the at least one image using a first color filtering; and
        ascertain, in a second step, a second value of the selected parameter one of: (i) without using the first color filter, or (ii) using the second color filter; and
    a comparator configured to compare the ascertained first and second values by determining a difference between the ascertained first and second values, and perform the one of detection, density determination, or classification of the aerosol as a function of the difference,
wherein:
    the selected parameter is one of the average brightness value or the gradient of the pixels, the difference is compared to a first threshold value and a second threshold value higher than the first threshold value, and the aerosol is one of detected or classified if the difference is higher than the first threshold value and lower than the second threshold value.

11. The device as recited in claim 10, wherein the first color filtering determines a red portion of the at least one image, and an absence of the first color filtering determines a gray portion of the at least one image.

12. The device as recited in claim 10, wherein the aerosol is illuminated using vehicle headlights, and the spectral characteristic of the vehicle headlights is taken into account in the one of detection, density determination, or classification of the aerosol.

13. The device as recited in claim 12, wherein the device subjects the result of the comparison to a second comparison against a predetermined expected result for the case of non-presence of an aerosol.

14. The device as recited in claim 10, wherein the ascertainment of the first and second values of the selected parameter takes place by taking into account only a selected portion of the image.

15. The device as recited in claim 14, wherein the selection of the selected portion of the image satisfies at least one of the following conditions: (i) the selected portion includes best illumination by the headlight; (ii) the location of the selected portion of the image is changed depending on the steering angle; and (iii) the selected portion of the image is set corresponding to the surface topology of the scenery located in the image.

16. The device as recited in claim 10, wherein the device checks the aerosol detection for plausibility using additional data.

17. A device for performing one of detection, density determination, or classification of an aerosol in an environment using at least one image of the environment taken by a camera of a vehicle, comprising:

a parameter determination unit having at least a first color filter and a second color filter different from the first color filter, wherein the parameter determination unit is configured to:

ascertain, in a first step, a first value of a selected parameter of the at least one image using a first color filtering; and ascertain, in a second step, a second value of the selected parameter one of: (i) without using the first color filter, or (ii) using the second color filter; and a comparator configured to determine a difference between the ascertained first and second values, and perform the one of detection, density determination, or classification of the aerosol as a function of the difference, wherein the selected parameter is one of the average brightness value or the gradient of the pixels, wherein the aerosol is illuminated using vehicle headlights, and the spectral characteristic of the vehicle headlights is taken into account in the one of detection, density determination, or classification of the aerosol, and wherein a convolution of the spectrum of the headlight with absorption characteristic of at least one possible aerosol is carried out, and the aerosol is detected as a function of the convolution.

* * * * *